US005562627A

United States Patent [19]
Chen

[11] Patent Number: 5,562,627
[45] Date of Patent: Oct. 8, 1996

[54] SAFETY SYRINGE WITH RETRACTABLE SELF-BIASED NEEDLE FOR INTRAVENOUS INJECTION WITHOUT PACKING RING

[76] Inventor: Long-Hsiung Chen, P.O. Box 55-1670, Taipei, Taiwan

[21] Appl. No.: 552,733

[22] Filed: Nov. 3, 1995

[51] Int. Cl.⁶ .................................................. A61M 5/00
[52] U.S. Cl. ........................................ 604/110; 604/195
[58] Field of Search ..................................... 604/110, 195, 604/192, 187, 263

[56] References Cited

U.S. PATENT DOCUMENTS

| | | | |
|---|---|---|---|
| 5,242,402 | 9/1993 | Chen | 604/110 |
| 5,431,632 | 7/1995 | Lu | 604/110 |
| 5,458,576 | 10/1995 | Haber et al. | 604/110 |

*Primary Examiner*—John D. Yasko

[57] ABSTRACT

A safety syringe for intravenous injection includes: a hollow needle normally eccentrically held in a sleeve portion formed on a front portion of a syringe, a suction tube replaceably mounted on the sleeve portion for sucking liquid medicine from an ampoule into the syringe, a plunger straightly slidably held in the syringe for injection use, a coupling member retained in the plunger engageable with a biasing socket recessed in a rear needle portion of the hollow needle with the biasing socket, whereby upon pushing of the plunger to the needle by forcibly inserting the coupling member into the biasing socket of the needle when finishing the injection, the biasing socket will be forcibly coupled with the coupling member, and upon retraction of the plunger and the needle into the syringe, the needle will be automatically inclined to prevent an outward protruding of the retracted needle from the syringe for preventing its pricking to the others; with the hollow needle annularly formed with a ratchet-tooth recess in a shank portion of the hollow needle to be engaged with a ratchet tooth annularly formed in an inside surface of the sleeve portion, thereby preventing an outward forward ejection of the hollow needle during the injection, and allowing a smooth rearward releasing of the hollow needle from the sleeve portion to be retracted into the syringe after the injection.

3 Claims, 5 Drawing Sheets

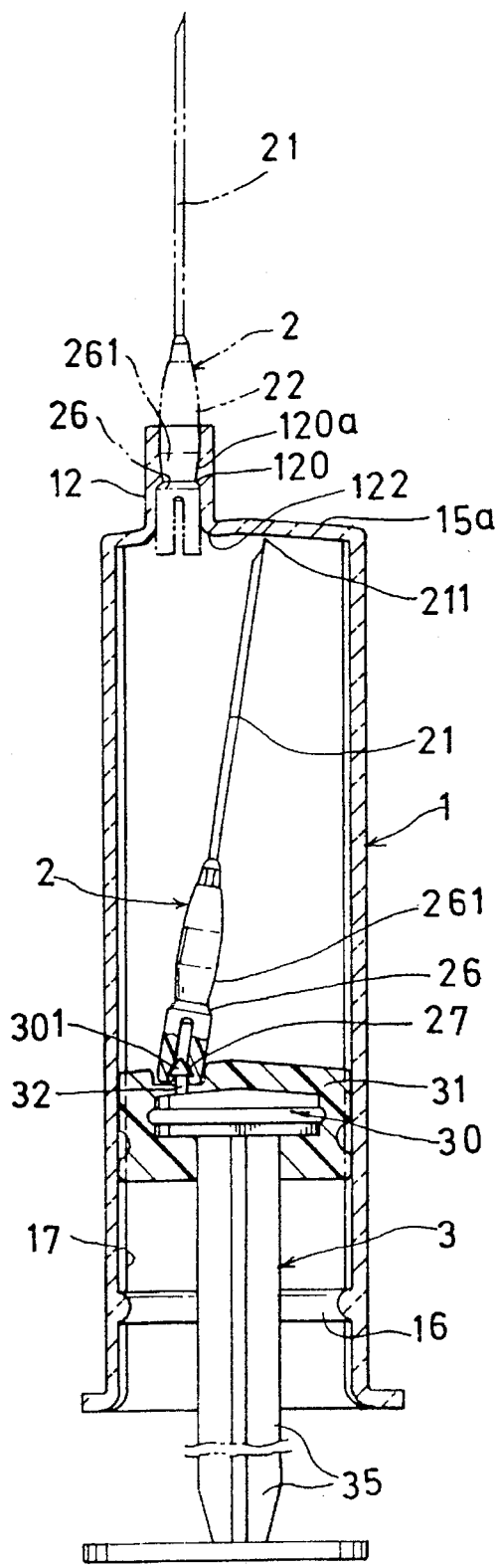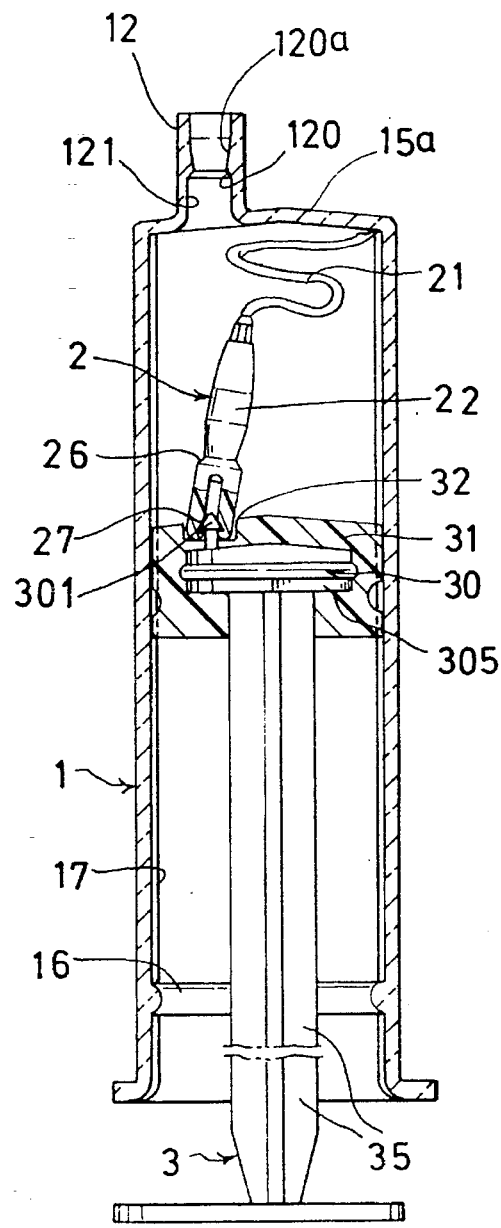
FIG.3
FIG.4

5,562,627

1

SAFETY SYRINGE WITH RETRACTABLE SELF-BIASED NEEDLE FOR INTRAVENOUS INJECTION WITHOUT PACKING RING

BACKGROUND OF THE INVENTION

U.S. Pat. No. 5,328,475 (hereinafter called prior art) granted to the same inventor of this application discloses a safety syringe in which the needle, as coupled with the plunger after finishing an injection, will be retracted into a syringe cylinder and will be automatically inclined to prevent its outward re-protrusion for safety purpose.

The shank portion 22 of the needle device 2 of the prior art is generally formed as a cylindrical shape and has a packing ring 26 fastened on the shank portion and engaged with a ring groove 120 recessed in the sleeve portion 12 of the syringe means 1.

When pushing the plunger 31 forwardly for performing an injection, the needle 2 may be accidentally ejected outwardly as subjected to the pressure of the boosted liquid medicine 4 within the syringe cylinder.

Therefore, the present inventor has invented a mechanism for preventing an unexpected ejection of the needle from the syringe during the injection as described hereinafter.

SUMMARY OF THE INVENTION

The object of the present invention is to provide a safety syringe for intravenous injection including: a hollow needle normally eccentrically held in a sleeve portion formed on a front portion of a syringe, a suction tube replaceably mounted on the sleeve portion for sucking liquid medicine from an ampoule into the syringe, a plunger straightly slidably held in the syringe for injection use, a coupling member retained in the plunger engageable with a biasing socket recessed in a rear needle portion of the hollow needle, whereby upon pushing of the plunger to the needle by forcibly inserting the coupling member into the biasing socket of the needle when finishing the injection, the biasing socket will be forcibly coupled with the coupling member, and upon retraction of the plunger and the needle into the syringe, the needle will be automatically inclined inwardly towards a blocking shoulder portion of the syringe when the needle is restored by the coupling member in the plunger by snugly engaging the coupling member with the biasing socket to prevent an outward protruding of the retracted needle from the syringe for preventing its pricking to the others; with the hollow needle annularly formed with a ratchet-tooth recess in a shank portion of the hollow needle to be engaged with a ratchet tooth annularly formed in an inside surface of the sleeve portion, thereby preventing a forward ejection of the hollow needle from the syringe during the injection, and allowing a smooth rearward releasing of the hollow needle from the sleeve portion to be retracted into the syringe after the injection.

BRIEF DESCRIPTION OF THE DRAWINGS

FIG. 3 shows the retraction of the needle into the syringe of the present invention.

FIG. 4 shows a bent needle in the syringe in accordance with the present invention.

2

Figure 5:
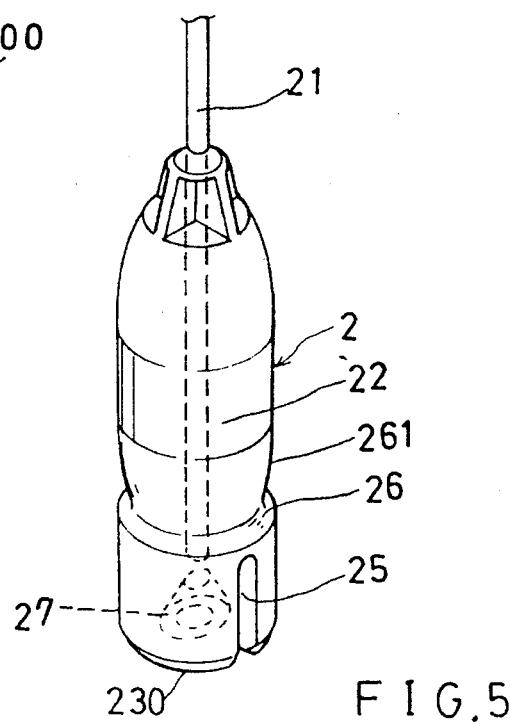

FIG. 5 is an illustration showing the needle of the present invention.

Figure 6:
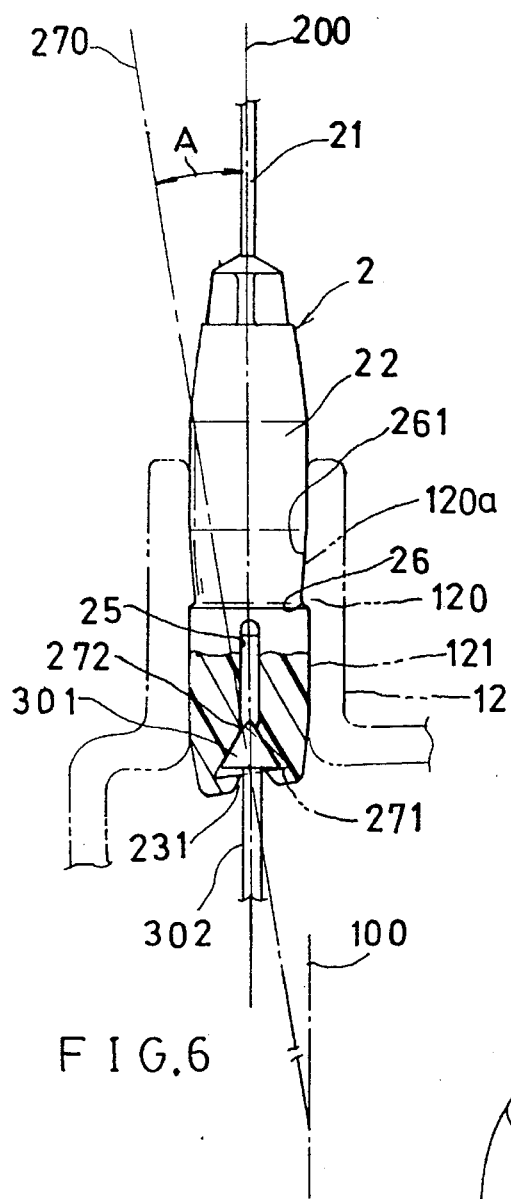

FIG. 6 shows a coupling member coupled with a rear needle portion in accordance with the present invention.

Figure 7:
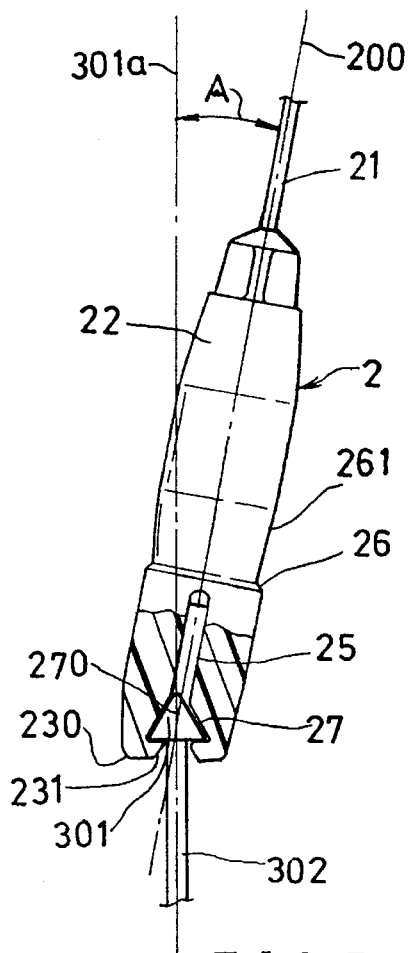

FIG. 7 shows an inclined needle when retracted in the syringe of the present invention.

Figure 8:
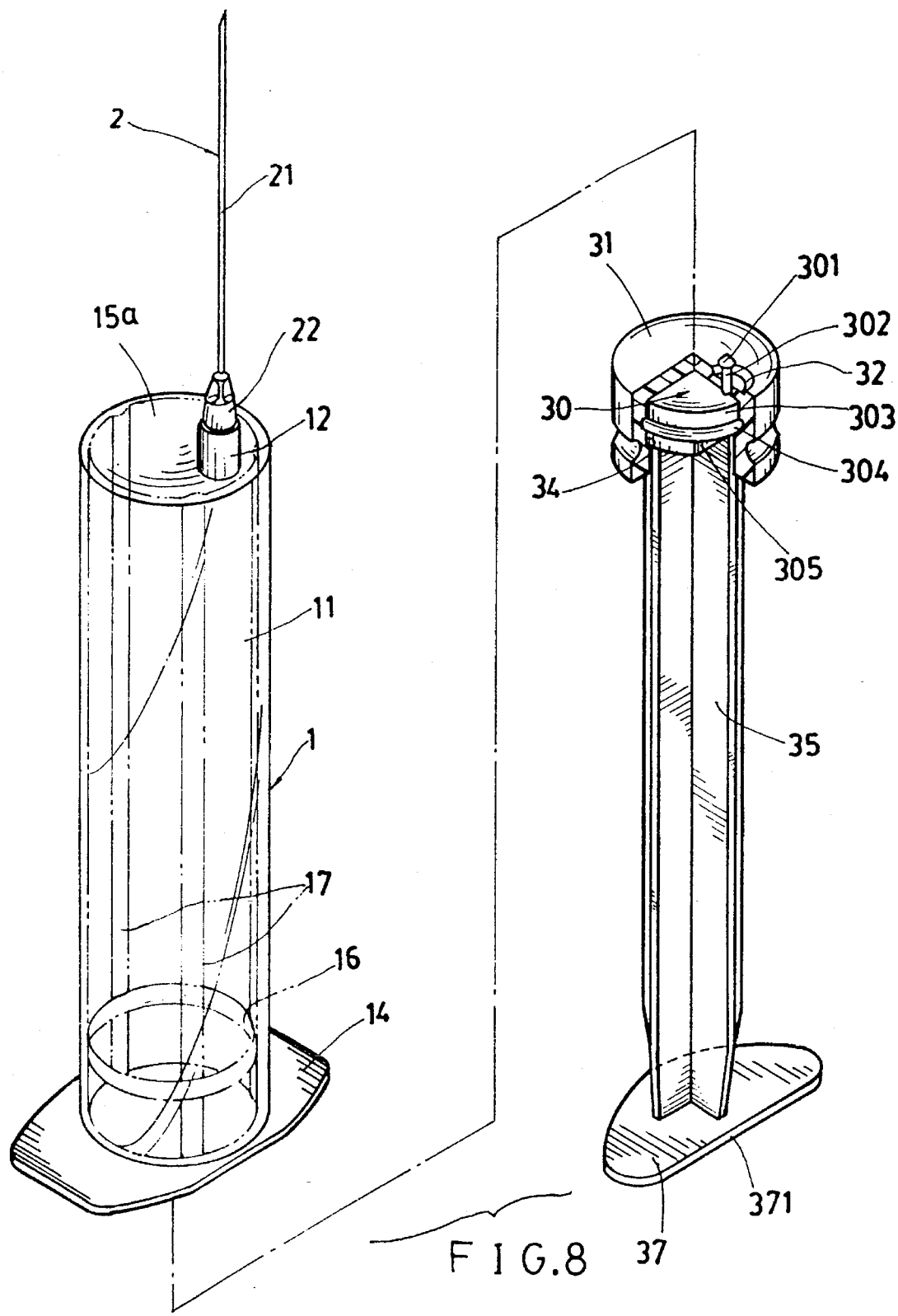

FIG. 8 is a perspective view of the present invention before being assembled.

Figure 9:
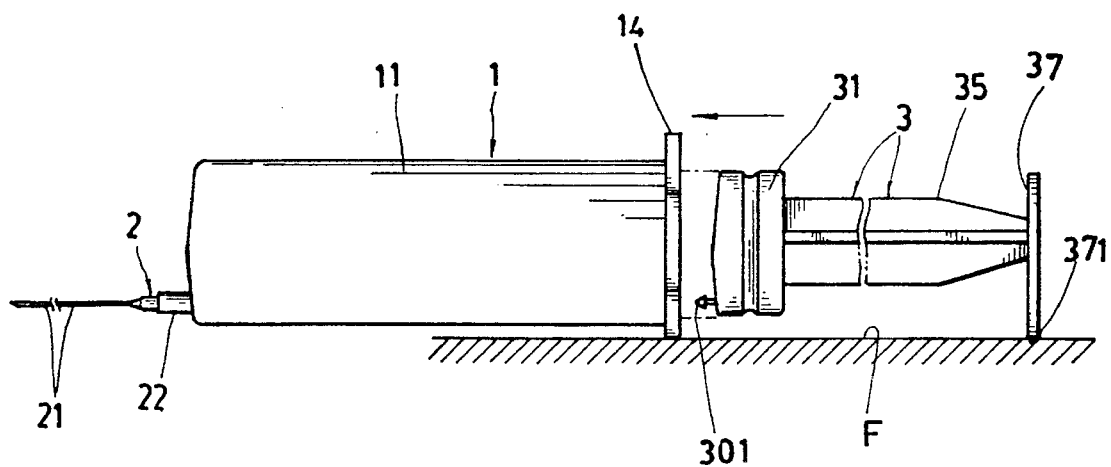

FIG. 9 shows an assembly of the present invention.

Figure 2:
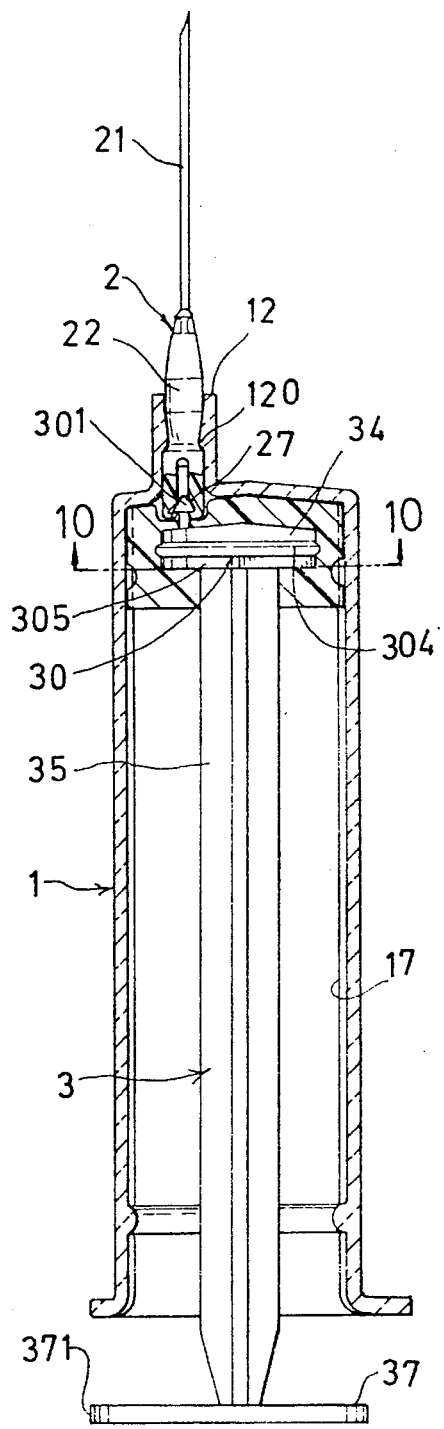
FIG. 2 shows coupling of the plunger with the needle when finishing a medical injection.
Figure 10:
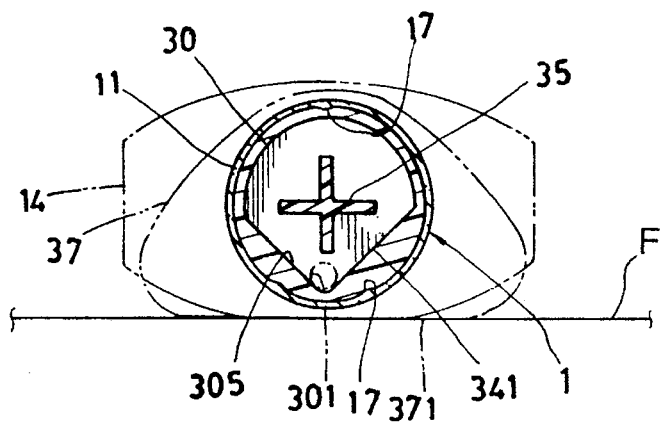

FIG. 10 is a sectional drawing as viewed from direction 10—10 of FIG. 2.

DETAILED DESCRIPTION

As shown in the drawing figures, the present invention comprises: a syringe means 1, a needle device 2, and a plunger means 3.

The syringe means 1 includes: a syringe cylinder 11 having a hollow bore portion 10 defined in the syringe cylinder 11 for filling liquid medicine 4 in the cylinder 11 and a syringe axis 100 longitudinally existing in a central portion of the syringe cylinder 11, a sleeve portion 12 eccentrically formed on a front side portion of the syringe cylinder 11 contracted forwardly from the cylinder 11 having a central opening 121 formed through the sleeve portion 12, and a diverging port 122 formed in a rear portion of the sleeve portion 12 adjacent to the syringe cylinder 11, a syringe handle 14 formed on a rear end portion of the cylinder 11, a blocking shoulder portion 15a formed at a rear end portion of the sleeve portion 12 and positioned between the central opening 121 of the sleeve portion 12 and the bore portion 10 of the syringe cylinder 11, an annular extension 16 annularly formed on a rear portion of the cylinder 11, a plurality of longitudinal rail extensions 17 longitudinally formed on an inside wall of the syringe cylinder 11, and the sleeve portion 12 having a ratchet tooth 120 annularly formed on an inside surface of the central opening 121 of the sleeve portion 12, and having an inside conical sloping surface 120a diverging forwardly from the ratchet tooth 120 in the sleeve portion 12.

The needle device 2 includes: a needle portion 21 having a needle tip 211 formed at a front end of the needle portion 21, a shank portion 22 connected with the needle portion 21, a bifurcated slot 25 longitudinally formed in a rear portion of the shank portion 22 and recessed forwardly from a rear needle end portion 230, a biasing socket 27 generally conical shaped formed in a rear portion of the shank portion 22 and communicating with a guiding port 231 recessed forwardly from the rear needle end portion 230, and a needle axis 200 longitudinally existing in a central portion of the needle device 2, with the shank portion 22 and the rear needle end portion 230 made of resilient plastic materials; and the shank portion 22 of the needle device having a ratchet-tooth groove 26 annularly recessed in the shank portion 22 to be engaged with the ratchet tooth 120 formed in the sleeve portion 12, and a conical sloping surface 261 circumferentially tapered rearwardly on the shank portion 22 towards the ratchet-tooth groove 26 to be engaged with the inside conical sloping surface 120a formed in the sleeve portion 12.

The needle axis 200 is parallel to the syringe axis 100 when the needle device 2 is normally secured on a sleeve portion 12 of the syringe means 1 for injection purpose.

Figure 1:
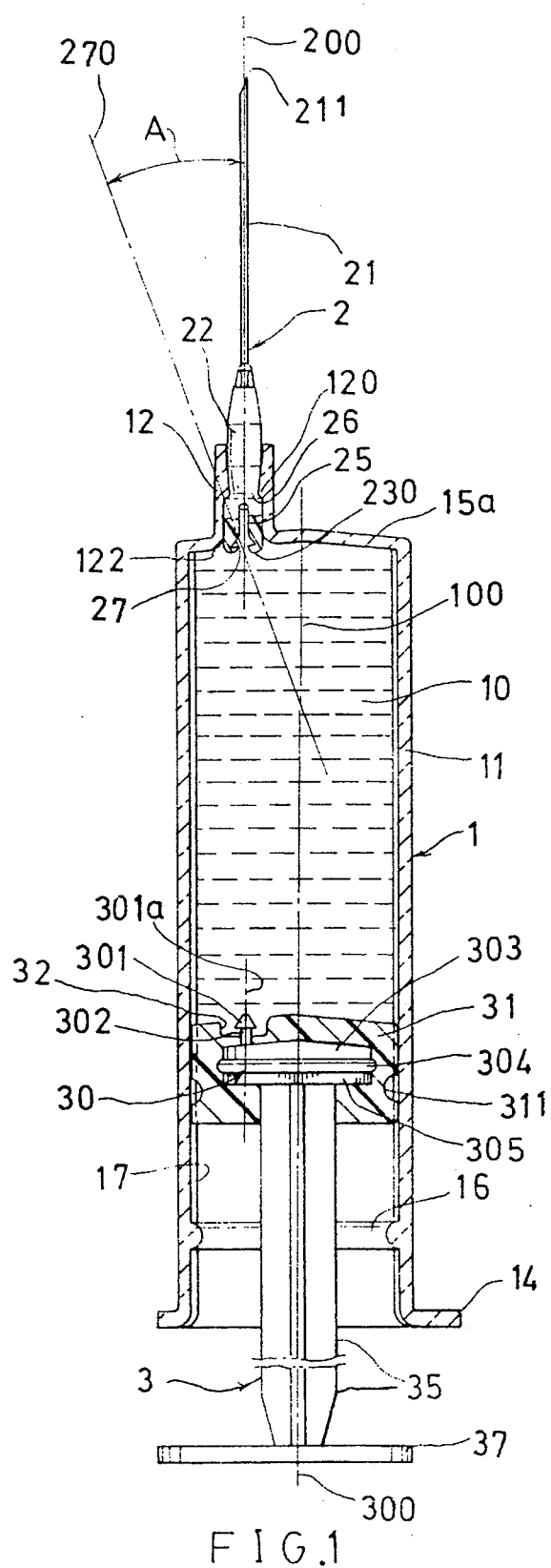
FIG. 1 is an illustration showing the present invention ready for injection use.

The biasing socket 27 generally conical shaped includes: a conical bottom 271, a conical apex 272 tapered forwardly from the conical bottom 271, and a longitudinal conical axis 270 aligned with the conical apex 272 to De perpendicular to the conical bottom 271 and to be outwardly inclinedly deviated from the needle axis 200 of the needle device 2 to define an acute angle A between the needle axis 200 and the longitudinal conical axis 270 of the biasing socket 27. The conical axis 270 is eccentrically deviated from the syringe axis 100 and interpolatively intersects the syringe axis 100 with the same acute angle A as shown in FIGS. 1 and 6. The biasing socket 27 is snugly engageable with an arrowhead portion 301 of the plunger means 3 for obliquely biasing the needle device 2 when coupled to the plunger means 3 and retracted in the syringe cylinder 11 after finishing an injection.

The plunger means 3 includes: a plunger 31 slidably held in the syringe cylinder 11 of the syringe means 3, a coupling member 30 retained in a coupling-member recess 34 in the plunger 31 having the arrowhead portion 301 eccentrically formed on a front end of the coupling member 30 operatively insertable in a biasing socket 27 formed in the needle device 2, a holding socket 32 concentrically disposed around the arrowhead portion 301 for operatively coupling a rear needle end portion 230 when bifurcated by the arrowhead portion 301 inserted into the biasing socket 27, with the rear needle end portion 230 confined within a diverging port 122 formed in a rear portion of a sleeve portion 12 of the syringe means 1, a plunger rod 35 having a plunger handle 37 protruding rearwardly from the plunger 31 for pushing operation of the plunger 31 with the plunger 31 formed with an annular recess 311 in the plunger 31 to be engaged with an annular extension 16 formed in a rear portion of the syringe cylinder 11 for restricting a rear movement of the plunger 31, and a plunger axis 300 longitudinally defined in a central portion of the syringe means 3 normally parallel to a needle axis 200 of the needle device 2 and also parallel to an arrowhead axis 301a of the arrowhead portion 301, and aligned with the syringe axis 100 of the syringe means 1.

The coupling member 30 includes: the arrowhead portion 301 being conical shaped and engageable with the biasing socket 27 which is formed as conical shape in the needle device 2 having the arrowhead axis 301a of the arrowhead portion 301 aligned with the needle axis 200 and parallel to the plunger axis 300 and parallel to the syringe axis 100 as shown in FIG. 1 ready for a normal medical injection, a neck portion 302 connected with the arrowhead portion 301, a base portion 303 having an annular protrusion 304 circumferentially formed on a periphery of the base portion 303 for well sealable embedding of the base portion 303 in the recess 34 in the plunger 31, and a secant block portion 305 engaged with a secant recess 341 formed at a rear end of the coupling-member recess 34 with the secant block portion 305 secured to a plunger rod 35 of the plunger means 3.

The plunger handle 37 has a flat bottom edge 371 slidably laid on a flat surface F as shown in FIG. 9 for a straight movement of the plunger means 3 in the syringe means 1 for sharply aiming the arrowhead portion 301 at the biasing socket 27 of the needle device 2 as shown in FIGS. 9, 10 and 2 since the plunger 31 will not be rotated as slidably engageable with the plural longitudinal rail extensions 17 formed in the syringe cylinder 11. The secant block portion 305 engaged with the secant recess 341 also enforce such a straight forward movement of the plunger 31 in the cylinder 11.

When using the present invention for injection use as shown in FIG. 1, the plunger 31 may be pushed forwardly to boost the medicine 4 in the cylinder 11 through the needle device 2 to a patient's body for an intravenous injection by inserting the eccentrically positioned needle device 2 to the patient's blood vessel.

The arrowhead portion 301 of the coupling member 30 will then be forcibly inserted into the biasing socket 27 of the needle device 2 to squeeze, and expansively bifurcate the rear needle portion 230 of the needle device 2 to store a resilient potential energy of the bifucated rear needle portion, thereby operatively coupling the coupling member 30 with the needle device 2 as shown in FIGS. 2, 6.

After retracting the plunger 31 and the coupled needle device 2 into the bore portion 10 of the syringe cylinder 11 as shown in FIG. 3, the biasing socket 27 of the needle device 2 will be restored to be snugly engaged with the arrowhead portion 301 of the coupling member 30 of the plunger means 3 by releasing a resilient force accumulated on the rear needle portion 230 when forcibly coupling the arrowhead portion 301 with the biasing socket 27 as shown in FIGS. 2 and 6, thereby automatically obliquely biasing the needle device 2 coupled on the plunger 31 to intersect the syringe axis 100 and orienting the needle device towards the blocking shoulder portion 15a as shown in FIGS. 7 and 3. After re-protruding the needle device 2 outwardly, the needle tip 211 will be retarded against the blocking shoulder portion 15a formed in a front portion of the cylinder 11 (FIG. 4), thereby bending the needle 2 and obstructing its outward protrusion and preventing its injury or contamination to the surroundings.

The present invention is superior to the earlier invention, U.S. Pat. No. 5,328,475 issued to the same inventor of this application because of the stable engagement of the needle device 2 on the sleeve portion 12 for injection.

Upon injection of the liquid medicine 4 in the syringe cylinder 11 under injection to pressurize the needle device, the ratchet tooth 120 in the sleeve portion 12 of the syringe means 1 will retard the ratchet-tooth groove 26 of the shank portion 22 of the needle device 2 to prevent an outward forward ejection of the needle device 2 from the sleeve portion 12 of the syringe means 1; and upon retraction of the needle device 2 as coupled on the plunger 31 into the syringe cylinder 11 after the injection, the conical sloping surface 261 of the shank portion 22 of the needle device 2 will be rearwardly thrusted along the inside conical sloping surface 120a in the sleeve portion 12 for a smooth retraction of the needle device 2 into the syringe cylinder 11 for reliable retraction of the used needle 2. The slope of the sloping surfaces 261, 120a has a very small sloping rate. Meanwhile, the sleeve portion 12 and the needle device 2 are made of plastic material having elastic property for a smooth engagement and disengagement between the sleeve portion 12 and the needle device 2, also for a better packing or sealing to prevent liquid leakage in between the needle device 2 and the sleeve portion 12.

The present invention may be modified without departing from the spirit and scope of this invention.

I claim:

1. A safety syringe for intravenous injection comprising:
   a syringe means (1) including a syringe cylinder (11) for filling liquid medicine (4) therein, a sleeve portion (12) eccentrically formed on a front portion of said syringe means (1) having a central opening (121) formed through the sleeve portion (12) and a syringe axis (100) longitudinally defined in a central portion of said syringe means (1);
   a needle device (2) including: a needle portion (21), a shank portion (22) connected with the needle portion (21) and held in the sleeve portion (12), a bifurcated slot (25) longitudinally formed in a rear portion of the shank portion (22) and recessed forwardly from a rear needle end portion (230), a biasing socket (27) generally conical shaped and formed in a rear portion of the shank portion (22) and communicating with a guiding port (231) recessed forwardly from the rear needle end portion (230), and a needle axis (200) longitudinally defined in a central portion of the needle device (2), with the shank portion (22) and the rear needle end portion (230) made of resilient plastic materials, said biasing socket (27) having a longitudinal conical axis (270) outwardly obliquely deviating an acute angle (A) from a needle axis (200) which is longitudinally defined in a central portion of said needle device (2) and is parallel to the syringe axis (100) of said syringe means (1); and a plunger means (3) including a plunger (31) slidably held in said syringe cylinder (11) for boosting liquid medicine (4) in said cylinder (11) for injection through said needle device (2), and a coupling member (30) embedded in said plunger (31) having an arrowhead portion (301) eccentrically formed at a front end of said coupling member (30) projectively aiming at said biasing socket (27) in said needle device (2) and operatively forcibly inserted in said biasing socket (27) to couple the arrowhead portion (301) with the needle device (2) after finishing an injection, and upon retraction of the plunger (31) and the needle device (2) coupled to said plunger (31) into said syringe cylinder (11), said needle device (2) will be automatically restored and obliquely biased inwardly to intersect the syringe axis (100) towards a front shoulder portion (15a) of said syringe cylinder (11) to prevent outward re-protruding of said needle device (2) from said syringe means (1);

the improvement which comprises:

said shank portion (22) of said needle device (2) having a ratchet-tooth groove (26) annularly recessed in said shank portion (22), and a conical sloping surface (261) circumferentially tapered rearwardly on said shank portion (22) towards the ratchet-tooth groove (26); and said sleeve portion (12) having a ratchet tooth (120) annularly formed on an inside surface of the central opening (121) of said sleeve portion (12) and engageable with said ratchet-tooth groove (26) recessed in said shank portion (22) of said needle device (2), and having an inside conical sloping surface (120a) diverging forwardly from said ratchet tooth (120) in said sleeve portion (12) and engageable with said conical sloping surface (261) of said shank portion (22) of said needle device (2), whereby upon injection of the liquid medicine (4) in said syringe cylinder (11) to pressurize said needle device (2), said ratchet tooth (120) in said sleeve portion (12) of said syringe means (1) will retard said ratchet-tooth groove (26) of said shank portion (22) of said needle device (2) to prevent an outward forward ejection of said needle device (2) from said sleeve portion (12) of said syringe means (1); and upon retraction of said needle device (2) as coupled on said plunger (31) into said syringe cylinder (11) after the injection, said conical sloping surface (261) on said shank portion (22) of said needle device (2) will be rearwardly thrusted along said inside conical sloping surface (120a) in said sleeve portion (12) for a smooth retraction of said needle device (2) into said syringe cylinder (11).

2. A safety syringe according to claim 1, wherein said syringe means (1) includes a plurality of longitudinal rail extensions (17) longitudinally formed inside the syringe cylinder (11) for slidably straightly engaging said plunger (31) of said plunger means (3) in said syringe cylinder (11).

3. A safety syringe according to claim 1, wherein said plunger means (3) includes a plunger handle (37) protruding rearwardly from said plunger (31) having a flat bottom edge (371) formed on said plunger handle (37) to be slidably movable on a flat surface (F); and said coupling member (30) having at least a secant block portion (305) formed on said coupling member (30) and engaged with at least a secant recess (341) recessed in a coupling-member recess (34), which is formed in the plunger (31) for retaining said coupling member (30) in said coupling-member recess (34), whereby upon a straight forward movement of said plunger (31) within said syringe cylinder (11), said plunger (31) will not be free rotated for an engagement of said arrowhead portion (301) of said coupling member (30) with said biasing socket (27) in said needle device (2).

* * * * *